United States Patent [19]

Wagaman et al.

[11] Patent Number: 5,041,661

[45] Date of Patent: Aug. 20, 1991

[54] METHOD OF PRODUCING TRIAMINOGUANIDINE NITRATE

[75] Inventors: Kerry L. Wagaman; Chester F. Clark, both of Waldorf, Md.; Larry D. Henderson, San Jose, Calif.

[73] Assignee: The United States of America as represented by the Secretary of the Navy, Washington, D.C.

[21] Appl. No.: 626,796

[22] Filed: Jul. 2, 1984

[51] Int. Cl.$^5$ .............................................. C07C 133/10
[52] U.S. Cl. ............................ 564/227; C07C/133/10
[58] Field of Search ........................................ 564/227

[56] References Cited

U.S. PATENT DOCUMENTS

| | | | |
|---|---|---|---|
| 3,950,421 | 4/1976 | Haury | 564/227 |
| 4,472,214 | 9/1984 | Flanagan et al. | 149/36 |
| 4,479,917 | 10/1984 | Rothgery et al. | 252/390 |
| 4,800,232 | 1/1987 | Rothgery et al. | 564/227 |

*Primary Examiner*—Edward A. Miller
*Attorney, Agent, or Firm*—Kenneth E. Walden; Roger D Johnson

[57] ABSTRACT

A process for preparing triaminoguanidine nitrate from relatively impure (90-99 percent)/commercial guanidine nitrate and commercial grade aqueous hydrazine (50-64 weight percent) in alcohol by: (1) adding enough hydrazine to form monoaminoguanidine nitrate, diaminoguanidine nitrate, or mixtures thereof, (2) physically removing the alcohol insoluble, solid impurities from the solution, (3) adding the remainder of the hydrazine needed to form triaminoguanidine nitrate, (4) adding nitric acid to adjust the pH to from 4.5 to 5.5, and (6) isolating the product triaminoguanidine nitrate.

14 Claims, 1 Drawing Sheet

METHOD OF PRODUCING TRIAMINOGUANIDINE NITRATE

BACKGROUND OF THE INVENTION

This invention relates to energetic organic nitrate compounds and more particularly to triaminoguaniddine nitrate.

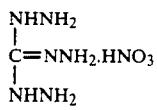

has been found to be an extremely useful ingredient in gun propellants. Unfortunately, the prior art methods of producing TAGN have not been satisfactory. Conventionally, TAGN has been produced by the following reactions:

(1) from calcium cyanamide:

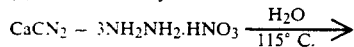

$$TAGN + Ca(NO_3)_2 + 2NH_3$$

(2) from cyanamide:

(3) from dicyanide:

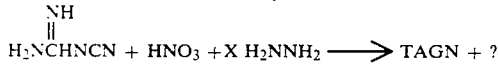

(4) from guanidine nitrate:

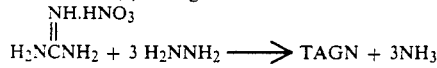

However, these techniques require high purity starting ingredients including pure, anhydrous hydrazine. Although these reactions typically provide yields of up to 80%, the product quality is poor and usually requires an expensive recrystallization. Also, the TAGN crystals are too large to use as a propellant ingredient and therefore they must be mechanically size-reduced.

SUMMARY OF THE INVENTION

Accordingly, an object of this invention is to provide a new method of preparing triaminoguanidine nitrate.

Another object of this invention is to reduce the cost of preparing triaminoguanidine nitrate.

A further object of this invention is to provide a method of preparing triaminoguanidine which does not require high purity starting materials.

Yet another object of this invention is to provide a method of preparing triaminoguanidine which produces a purer product which does not require expensive recrystallization.

A still further object of this invention is to provide a method which produces small crystals of triaminoguanidine nitrate thus eliminating the need for mechanical reduction of the particle size.

These and other objects of this invention are accomplished by providing:

A process for preparing triaminoguanidine nitrate by
(a) reacting guanidine nitrate with from 1 to 2 moles of hydrazine per mole of guanidine nitrate in alcohol to produce a solution of monoaminoguanidine nitrate, diaminoguanidine nitrate, or mixtures there of in alcohol;

(b) filtering the alcohol solution to remove alcohol insoluble solid impurities;

(c) adding additional hydrazine to bring the total amount of hydrazine added to 3 or slightly more moles per mole of guanidine nitrate used;

(d) adjusting the pH of the alcohol solution to from 4.5 to 5.5 by adding nitric acid; and (e) isolating the product triaminoguanidine nitrate.

Triaminoguanidine nitrate is useful as an ingredient in gun propellants.

BRIEF DESCRIPTION OF THE DRAWINGS

FIGS. 1 and 2 present experimental data and are discussed in detail in the Examples.

DETAILED DESCRIPTION OF THE INVENTION

The process of the present invention is designed to produce triaminoguanidine nitrate from guanidine nitrate (GN) and hydrazine at a lower cost than that of prior art procedures. The process can use low purity (91%), low cost, commercially available guanidine nitrate and low cost, commercially available aqueous hydrazine.

The major impurities in commercial grade guanidine nitrate are soluble in water but insoluble in alcohols. Guanidine nitrate is only slightly soluble and the product triaminoguanidine (TAGN) nitrate is insoluble in alcohols. However, the intermediates monoaminoguanidine nitrate (MAGN) and diaminoguanidine nitrate (DAGN) are soluble in alcohols.

Therefore a critical feature in the process of the present invention is the use of an alcohol as the reaction solvent. A second important feature is the use of only enough hydrazine to convert the guanidine nitrate to monoaminoguanidine nitrate, diaminoguanidine nitrate, or mixtures thereof. From 1 to 2 moles of hydrazine are added for each mole of guanidine nitrate.

Next, the solid impurities are physically removed from the solution. Common methods such as filtration or centrifugation are used for this purpose.

Finally, more hydrazine is added to convert the monoaminoguanidine and diaminoguanidine nitrates to the final product triaminoguanidine nitrate. Enough hydrazine is added to bring the total molar ratio of hydrazine to guanidine nitrate to 3:1 or slightly more. Nitric acid (e.g., 70% HN03 is added to adjust the pH of the reaction mixture to 4.5-5.5, or preferably about 5.

Purer TAGN was achieved by crystalline9 the triaminoeuanidine nitrate at ambient room temperature (20° C.) than with cooling (5° C.).

To eliminate the formation of oxidation products with air and the reaction solution, nitrogen is used to sparge the reaction solution and purge the air above the solution. Nitrogen need only be added at the initial and final stages of the reaction or during shutdowns. During the reaction, ammonia is generated which acts as an inert blanket gas.

The ammonia generated during the reaction also provides a convenient means of monitoring the progress of the reactions. At each of the reaction phases hydrazine is consumed and ammonia is generated:

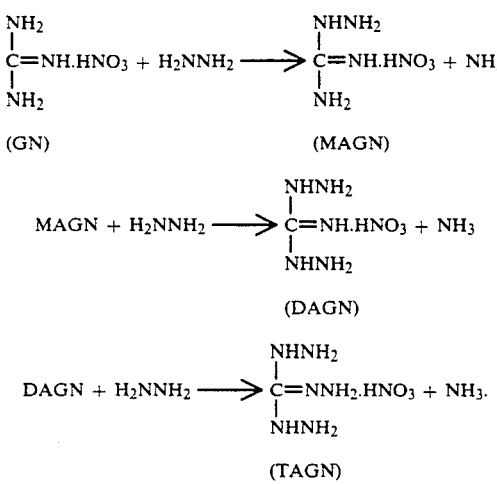

(GN) → (MAGN) → (DAGN) → (TAGN)

The use of low cost, commercially available aqueous solutions of hydrazines is an important feature of this invention. These commercially available solutions comprise from 50 to 64 weight percent of hydrazine. More concentrated hydrazine, even anhydrous, may be used in the process, but that would increase the cost without providing any significant advantage.

A critical feature of this invention is the use of an alcohol as the reaction solvent. Low cost, low molecular weight alcohols (1 to 5 carbons atoms) are used, with ethanol and 1-propanol being preferred, and 1-propanol being the most preferred alcohol. The volume of alcohol is sufficient to dissolve the monoaminoguanidine and diaminoguanidine nitrates formed and to negate or reduce the solubility effects of the water added to the reaction solution with the hydrazine. In general, from about 150 to about 300 grams of alcohol per mole (122 gm) of guanidine nitrate are used. These ratios can be scaled up as needed.

The reactions in the present process are preferably run at a temperature of from about 70° C to about 110° C and more preferably from 80° C to 100° C. Preferably the guanidine nitrate/alcohol slurry is heated up to the desired reaction temperature before the hydrazine is added.

The reaction mixture should be agitated (e.g., stirred) Vigorous agitation produces the best results. Note that during the initial step of the process, agitation is used to produce a suspension of the slightly soluble guanidine nitrate particles in alcohol.

The process has been tested at reduced pressure (10 to 110 mm Hg), but the best results are obtained at normal atmospheric pressure.

The general nature of the invention having been set forth, the following examples are presented as specific examples thereof. It will be understood that the invention is not limited to these specific examples but is susceptible to various modifications that will be recognized by one of ordinary skill in the art.

EXAMPLES 1 THRU 9

Several process variables were examined in the synthesis of triaminoguanidine nitrate (TAGN) made from the reaction of hydrazine with guanidine nitrate (GN). In all of the following examples the experiments were run in a 3-necked one liter round-bottomed flask heated with a heating mantle or immersed in a temperature-controlled hot water bath and equipped with a glass stirrer with a Teflon®blade, addition flask and a ice-water cooled condensor having a flow meter on its outlet. In all cases 122 grams (1 mole) of guanidine nitrate and 200 grams of solvent were initially added to the flask, the mixture was agitated and then 150 grams of 64% hydrazine in water was added. In some cases the initial reaction temperature was about 20° C. and then the reactants were heated up to a higher reaction temperature. In other cases the GN-solvent mixture was preheated to the higher temperature prior to the addition of the ambient temperature, aqueous hydrazine. The reactions were run until no additional ammonia was evolved, usually less than two hours, or were limited to a maximum of five hours. Table 1 summarizes the process variable values for these 9 examples and the results of these reaction conditions.

FIG. 1 shows the amount of ammonia (moles of NH₃ per mole of guanidine nitrate) released as a function of time for variations of the initial reaction temperature and for an initial addition of nitric acid in the synthesis of TAGN.using water as the solvent (examples 1 thru 3). Although the evolution of ammonia was initially lower for the first hour of reaction time for the lower temperature of the initial reactants, these reactions evolved almost 100% of the theoretical amount of ammonia.

| Example | Solvent | Initial Reaction Temperature | Final Reaction Temperature | Percent Yield Of TAGN | Color of TAGN | Comments |
| --- | --- | --- | --- | --- | --- | --- |
| 1 | Water | 20° C. | 102° C. | 63% | White | |
| 2 | Water | 20° C. | 100° C. | 69% | White | 0.46 moles of 70% nitric acid was added at the start of the reaction |
| 3 | Water | 95° C. | 95° C. | 57% | White | |
| 4 | Water | 20° C. | 40° C. | 44% | Lt. Orange | Reaction pressure was 10 mm Hg |
| 5 | Water | 20° C. | 55° C. | 33% | Lt. Yellow | Reaction pressure was 50 mm Hg |
| 6 | Water | 22° C. | 64° C. | 50% | White | Reaction pressure was 110 mm Hg |
| 7 | Water | 20° C. | 103° C. | 24% | Pink | Six moles of hydrazine were added |
| 8 | Ethanol | 80° C. | 80° C. | 95% | Pink | |

-continued

| Example | Solvent | Initial Reaction Temperature | Final Reaction Temperature | Percent Yield Of TAGN | Color of TAGN | Comments |
|---|---|---|---|---|---|---|
| 9 | 1-Propanol | 98° C. | 90° C. | 96% | Lt. Pink | |

The addition of the nitric acid improved the reaction yield from 63 to 69%.

In examples 4 thru 6 a partial vacuum was applied to the reactor to determine its effect on reaction yield. Although ammonia is more easily removed at the lower vacuum conditions, the boiling point of the reactants is also lowered; this lowers the maximum reaction temperature and therefore increases the reaction time and decreases the reaction yield and purity.

In example 7 a 100% excess of hydrazine was added to the reaction flask. This decreased the reaction yield from 63% (example 1) to 24%.

In examples 8 and 9, ethanol and 1-propanol were used respectively as the inert diluents. The effect of this solvent selection on the rate of reaction is compared with the use of water as the solvent in FIG. 2. Unlike water as a solvent, these alcohols gave much higher initial rates of reaction by having the reactants preheated to about 90° C. and also gave much higher product yields of 95 to 96% as compared to 57 to 69%. Either white or this pinkish discoloration of the TAGN is acceptable.

It should be emphasized that the normal undesirable impurities that are present in the guanidine nitrate are melamine and ammonium nitrate. Although these chemicals are water-soluble, they are alcohol insoluble. If one reacts from one to two moles of hydrazine with one mole of guanidine nitrate in an alcohol solvent system, the mono-and di-aminoguanidine nitrate (MAGN and DAGN) products are soluble in the alcohol system. By filtering these solutions at this time one can remove the insoluble ammonium nitrate and melamine. Then the total required amount of hydrazine can be added to complete this synthesis of TAGN.

Also, because of this solubility of MAGN and DAGN in alcohols, the final addition of this hydrazine can be done in a continuous crystallizer. One will be able to achieve the desired particles size distribution of the TAGN and avoid an expensive and hazardous mechanical size reaction of this explosive material.

Based on the above examples, table 2 summarizes the optimum reaction conditions for the synthesis of TAGN.

Obviously, numerous modifications and variations of the present invention are possible in light of the above teachings. It is therefore to be understood that within the scope of the appended claims the invention may be practiced otherwise than as specifically described herein.

TABLE 2

| OPTIMUM CONDITIONS FOR TAGN PRODUCTION | |
|---|---|
| REACTION TEMPERATURE | ≧ 80° C. |
| REACTION PRESSURE | ≧ 1 ATM |
| REACTION TIME | 1 HOUR |
| HYDRAZINE CONCENTRATION | 64% HYDRAZINE IN $H_2O$ |
| HYDRAZINE/GN RATIO | 3:1 |
| SOLVENT | 1-propanol |
| AGITATION | VIGOROUS |
| CRYSTALLIZATION TEMPERATURE | 20° C. |
| SOME $HNO_3$ SHOULD BE PRESENT | |

What is claimed as new and desired to be secured by Letters Patent of the United States is:

1. A process for preparing triaminoguanidine nitrate comprising the following steps in order:
   (1) forming a suspension of guanidine nitrate in an alcohol of from 1 to 5 carbon atoms by agitation;
   (2) adding from 1 to 2 moles of hydrazine for each mole of guanidine nitrate to the alcohol to form a reaction mixture;
   (3) heating the reaction mixture at a temperature of from about 70° C to about 110° C until all of the hydrazine has reacted with the guanidine nitrate;
   (4) filtering the reaction mixture to remove solid impurities;
   (5) adding enough hydrazine to the reaction mixture to bring the total amount added to three moles of hydrazine for each mole of guanidine nitrate used;
   (6) heating the reaction mixture at a temperature of from about 70° C to about 110° C until all of the hydrazine has reacted;
   (7) adjusting the pH of the reaction mixture to from 4.5 to 5.5 by adding nitric acid; and
   (8) isolating the product triaminoguanidine nitrate.

2. The process of claim 1 wherein the alcohol is selected from the group consisting of ethanol, 1-propanol and mixtures thereof.

3. The process of claim 2 wherein the alcohol used is 1-propanol.

4. The process of claim 1 wherein the hydrazine is added in the form of a 50 to 64 percent by weight aqueous hydrazine solution.

5. The process of claim 1 wherein the purity of the guanidine nitrate is from 90 to 99 percent.

6. The process of claim 1 wherein the reaction mixture is agitated during steps (2), (3), (5), and (6).

7. The process of claim 1 wherein the alcohol is heated up to a temperature of from about 70° C. to about 110° C. before the addition of the hydrazine in step (2).

8. The process of claim 1 wherein the reaction mixture is kept at a temperature of from 80° C. to 100° C. during step (3).

9. The process of claim 8 wherein the alcohol is heated up to a temperature of from 80° C. to 100° C. before the addition hydrazine in step (2).

10. The process of claim 1 wherein the reaction mixture is kept at temperature of from 80° C. to 100° C. during step (6).

11. The process of claim 1 wherein after step (6) small increments of hydrazine are added to the reaction solution until no ammonia is generated, the reaction mixture being kept at a temperature of from about 70° C. to about 110° C.

12. The process of claim 11 wherein the reaction temperature is kept at a temperature of from 80° C. to 100° C. while the small increments of hydrazine are being added after step (6).

13. The process of claim 1 wherein an inert atmosphere is used to prevent air oxidation of the reactants and products during the process.

14. The process of claim 13 wherein the inert atmosphere is a gas selected from the group consisting of nitrogen, ammonia, and mixtures thereof.

* * * * *